United States Patent [19]

Nevyas-Wallace

[11] Patent Number: 5,336,236

[45] Date of Patent: Aug. 9, 1994

[54] SURGICAL KNIFE AND METHOD FOR PERFORMING RADIAL KERATOTOMY ENHANCEMENT SURGERY

[76] Inventor: Anita S. Nevyas-Wallace, 231 Tower La., Narberth, Pa. 19072

[21] Appl. No.: 135,203

[22] Filed: Oct. 12, 1993

[51] Int. Cl.$^5$ .............................. A61B 17/32
[52] U.S. Cl. .................... 606/166; 606/167; 30/357; 128/898
[58] Field of Search ............ 606/166, 167, 170, 172; 30/294, 357; 128/898

[56] References Cited

U.S. PATENT DOCUMENTS

| | | | |
|---|---|---|---|
| 3,798,688 | 3/1974 | Wasson | 30/357 |
| 4,552,146 | 11/1985 | Jensen et al. | |
| 4,602,630 | 7/1986 | Anis | |
| 4,672,965 | 6/1987 | Baum | |
| 4,759,363 | 7/1988 | Jensen | |
| 4,884,569 | 12/1989 | Fedorov et al. | |
| 5,203,865 | 4/1993 | Siepser | 606/167 |
| 5,222,967 | 6/1993 | Casebeer et al. | 606/167 |

*Primary Examiner*—Stephen C. Pellegrino
*Assistant Examiner*—Wm. Lewis
*Attorney, Agent, or Firm*—Panitch Schwarze Jacobs & Nadel

[57] ABSTRACT

A surgical knife and a method for enhancing incisions in radial keratotomy enhancement surgery on an eye having a cornea and a central optical zone, where a generally radial incision previously made in the cornea has a wall adjacent the optical zone and is to be extended centripetally toward the optical zone. The knife comprises a knife blade with an end, and the blade has a sharpened cutting edge facing in a leading direction, a recess extending inwardly from the cutting edge and from the end of the blade, and a stopping edge and a measuring edge at the recess. The stopping edge faces in the leading direction. The measuring edge has a predetermined length and extends from the cutting edge to the stopping edge. The surgical knife is inserted into a previously made incision so that the cutting edge and the stopping edge face centripetally and the end of the blade contacts a bottom portion of the incision. The knife is advanced toward the optical zone, and the incision is extended a distance no greater than the predetermined length of the measuring edge. The surgical knife is then removed from the extended incision and the uneven bottom portion of the incision is evened out.

9 Claims, 2 Drawing Sheets

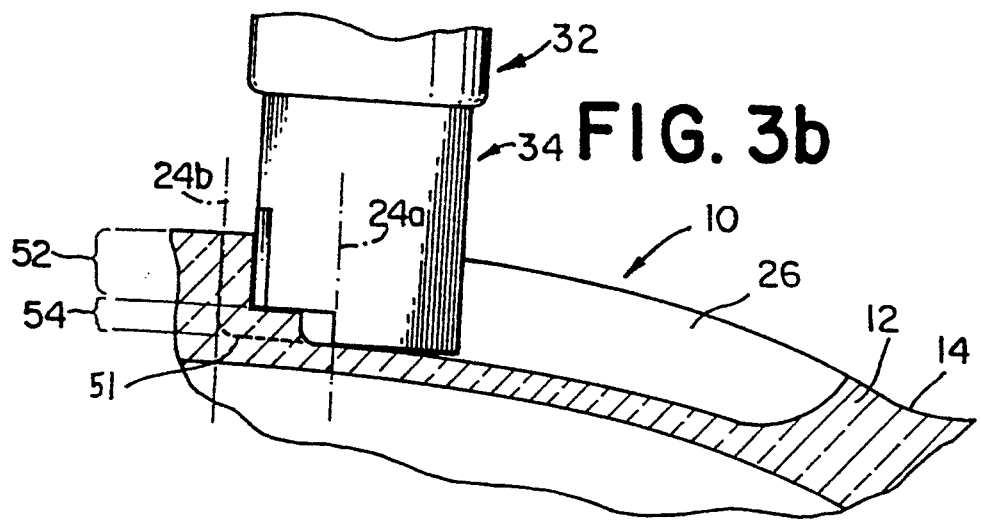
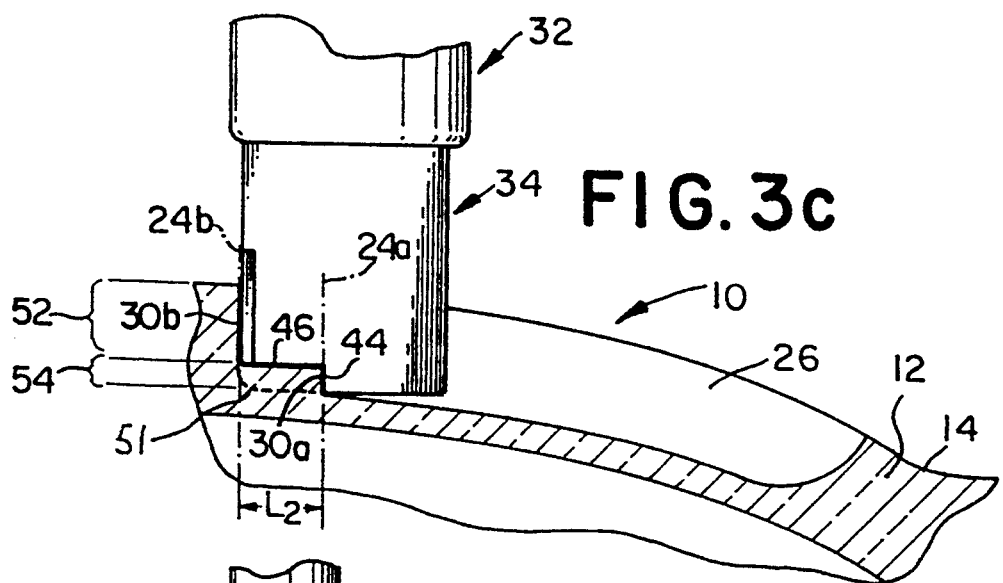
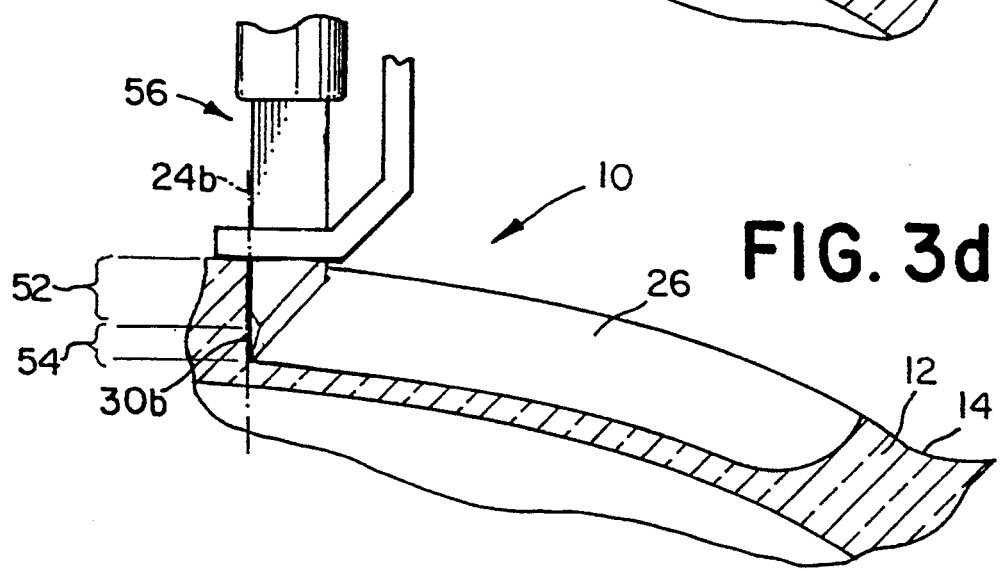

SURGICAL KNIFE AND METHOD FOR PERFORMING RADIAL KERATOTOMY ENHANCEMENT SURGERY

BACKGROUND OF THE INVENTION

The present invention relates to a surgical knife for use in eye surgery and a method for performing a radial keratotomy (RK) surgical procedure. More particularly, the invention relates to a knife design and a method which allow corneal incisions in an RK procedure to be precisely enhanced by extending precisely and safely the incisions centripetally.

The RK surgical procedure is performed to correct myopia (nearsightedness). In a typical initial procedure, a surgeon uses a surgical knife to make four to eight (or more) spoke-like radial cuts of a controlled depth in the paracentral and peripheral cornea to produce a flattening effect on the central cornea. Exact extension of incisions into the optical zone of the cornea and a precise depth of cut are important so that the correction of curvature of the cornea is not too great or too little.

Since an RK procedure involves cutting the cornea of a human eye, great care must be taken to ensure that the cuts are precise and at the depth necessary to provide for the indicated correction. Consistent results are difficult to achieve. A problem which has been known to occur is an under-correction of the myopia through cuts which are not as deep or long as required. Cuts are normally made conservatively because the knife is extremely sharp and many surgeons tend to be overcautious when the knife is close to the optical zone, the uncut central portion of cornea.

Inevitably, a certain percentage of RK procedures performed are not entirely successful in that the curvature of the cornea has not been flattened enough. In such a situation, a first enhancement procedure may be performed with an enhancement blade that is sharp only near the point of the blade. The enhancement blade is used in one or more selected incisions to even out the bottoms of the incisions and to square off the ends of the incisions adjacent to the optical zone at the center of the cornea. Oftentimes, the first enhancement procedure is carried out during the original operation.

If additional enhancement is required, most surgeons extend the incisions centripetally toward the center of the cornea. At least two basic procedures for extending an incision are used. In the Russian (centripetal) technique, a surgical knife starts in the initial incision and extends toward the center of the cornea. The Russian technique has the advantage of greater attained depth and a squarer cut end, resulting in greater correction. However, the Russian technique has a considerable disadvantage in that there is a danger of extending the incision too far towards the center of the cornea. In the American (centrifugal) technique, alternatively, a new incision is started at the end of the new smaller optical zone and extending outwardly to connect with the original incision. The American technique has an advantage in that the danger of cutting into the optical zone of the cornea is eliminated. The American technique, too, has a considerable disadvantage in that the new incision tends to be shallower and may not lie in line with and interconnect to the end of the original incision. In such a case, vision may become obscured, and the overlapping, parallel incisions exacerbate glare.

It would be advantageous to combine the safety of the American technique with the greater precision of the Russian technique.

SUMMARY OF THE INVENTION

The present invention is directed to a new blade for a surgical knife which is useful in enhancing incisions in RK surgery, and to a new method for forming such incisions. The blade can be designed to fit into a holder of a type presently used, which grabs the shank of the blade and secures the blade in place during surgery.

Briefly stated, the surgical knife is for use in radial keratotomy enhancement surgery on an eye having a cornea and a central optical zone, where a generally radial incision previously made in the cornea has a wall adjacent the optical zone and is to be extended centripetally toward the optical zone. The knife comprises a knife blade with an end, a sharpened cutting edge facing in a leading direction, a recess extending inwardly from the cutting edge and from the end of the blade, and a stopping edge and a measuring edge at the recess. The stopping edge faces in the leading direction. The measuring edge has a predetermined length and extends from the cutting edge to the stopping edge.

The method of performing radial keratotomy enhancement surgery requires inserting a surgical knife substantially as described above into a previously made incision so that the cutting edge and the stopping edge face centripetally and the end of the blade contacts a bottom portion of the incision. The knife is advanced toward the optical zone, and the incision is extended a distance no greater than the predetermined length of the measuring edge. The surgical knife is then removed from the extended incision and the uneven bottom portion of the incision is evened out with an enhancement blade sharp only at the distal 150 to 250 microns.

BRIEF DESCRIPTION OF THE DRAWINGS

The foregoing summary, as well as the following detailed description of a preferred embodiment of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings:

FIGS. 3a–3c are cross-sectional views of a section of a cornea wherein the surgical knife of the present invention is enhancing a previously made incision in accordance with the present invention;

FIG. 3d is a schematic view showing a knife blade flattening the bottom portion and squaring off the wall of the extended incision in accordance with the present invention.

DETAILED DESCRIPTION OF PREFERRED EMBODIMENTS

Figure 1:
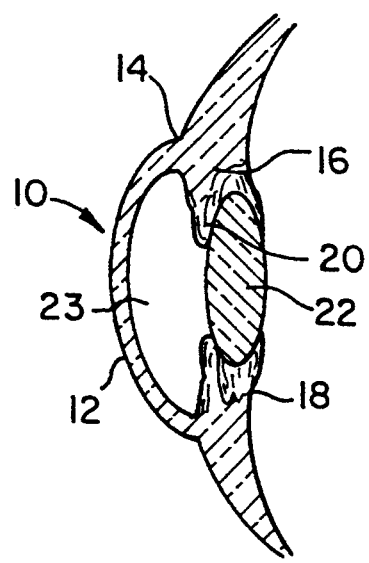
FIG. 1 is a cross-sectional view of a typical human eye showing, in particular, the cornea and other elements defining the anterior chamber.

Certain terminology may be used in the following description for convenience only and is not limiting.

The words "right", "left", "upper" and "lower" designate directions in the drawings to which reference is made. The words "inwardly" and "outwardly" are further directions toward and away from, respectively, the geometric center of the referenced element. The terminology includes the words above specifically mentioned, derivatives thereof, and words of similar import.

Referring to the drawings in detail, wherein like numerals are used to indicate like elements throughout, there is shown in FIG. 1 the anatomy of a human eye generally designated by reference numeral 10. Of course, one skilled in the art will recognize that the surgical knife and method to be described are not limited to a human eye, and may in fact be employed on any similar animal eye.

The outer surface of the eye 10 is formed by a cornea 12 which terminates at the corneal margin or limbus 14 in the vicinity of an anatomical protuberance on the inner surface of the cornea known as a scleral spur 16. A ciliary muscle 18 joins an iris 20 and is connected to a lens 22 which is caused by the ciliary muscle to flex in order to focus the vision of the subject. An anterior chamber 23 is defined by the space between the cornea 12 and the lens 22 and iris 20.

Figure 2:
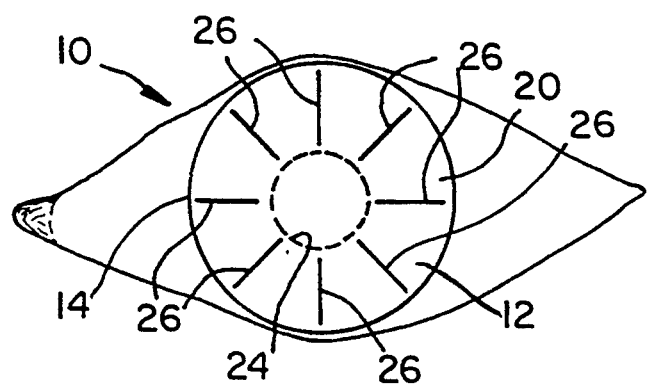
FIG. 2 is a front view of the human eye showing typical incisions made through an initial radial keratotomy surgical procedure.

Referring to FIG. 2, the optical zone illustrated by dotted lines 24 is the central uncut portion of the cornea through which light passes to the lens 22 and onto a retina (not shown) for transmission of an image to the optical nerve and brain. When a patient is myopic or nearsighted, the cornea tends to have a greater curvature than necessary, which causes the focal point of images entering the eye to be offset from the retina. It has been found that myopia can be surgically corrected by forming a number of incisions such as those designated by reference numeral 26 in FIG. 2 in the outer surface of the cornea 12, which have the effect of flattening the center of the cornea 12. Although FIG. 2 shows eight incisions 26, one skilled in the art will recognize that a number of incisions more or less than eight may be used, depending upon the particular circumstances. The incisions 26 preferably extend from the edge of the initial optical zone 24a (shown in FIG. 3a) to within 3,000 microns (micrometers) of the limbus 14. Various methods have been described in the prior art for forming the incisions 26. U.S. Pat. No. 5,222,967, hereby incorporated by reference, is illustrative.

As previously described, if in fact the initial refractive incision is not successful in flattening sufficiently the cornea 12, a first enhancement procedure may comprise the use of an enhancement blade to flatten out the bottom 28 of the incision 26 (as seen in FIGS. 3a–3d) and to square off the initial wall 30a of the incision 26 at the optical zone 24a.

Figure 3A:
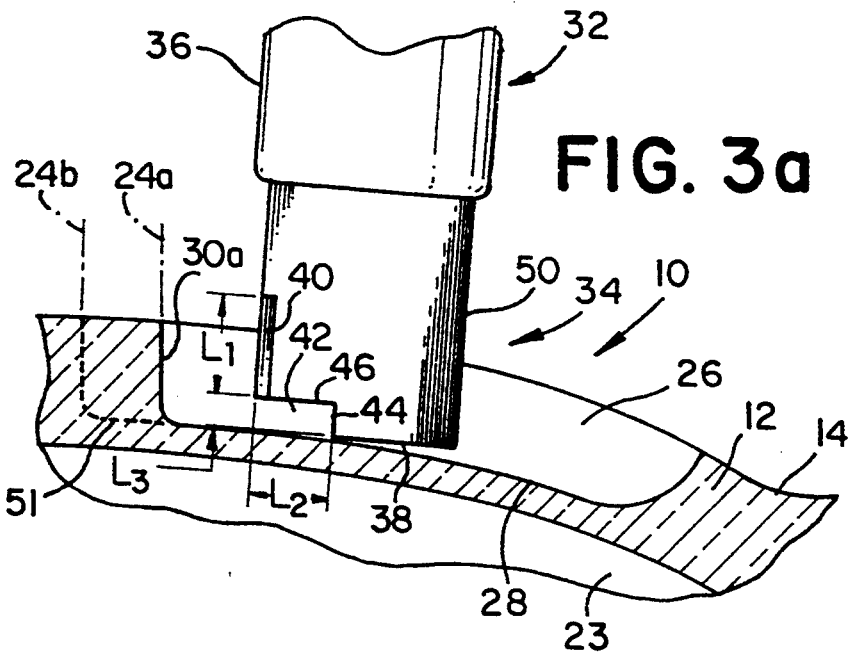

If the first enhancement procedure is not successful, or not necessary because it had been incorporated into the original operation, and the patient needs an additional enhancement procedure, the surgical knife 32 of the present invention, as shown in FIGS. 3a–3c, is used. The surgical knife 32 comprises a knife blade 34. As will be understood, the knife blade 34 may be attached to a handle or holding device 36 in any of a number of ways. Preferably, the knife blade 34 is a flat diamond knife blade having a generally rectangular shape, and is designed to fit into the handle 36. Also preferably, the handle 36 grabs the blade 34 at a shank (not shown) and securely holds the blade 34 in place during surgery.

Figure 4:
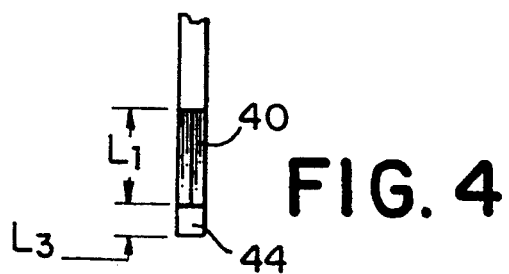
FIG. 4 is a partial front view of the surgical knife shown in FIGS. 3a–3c.

The knife blade 34 has a relatively dull distal edge or end 38 and a sharpened cutting edge 40. The cutting edge 40 is arranged to face in a leading direction. Since the initial radial incision 26 previously made in the cornea is to be extended centripetally toward the optical zone 24b, the leading direction would normally be toward the optical zone 24b. As shown in FIG. 4, the sharpened cutting edge 40 is formed by a pair of angled surfaces.

The knife blade 34 also has a generally rectangular recess 42. As shown in FIG. 3a–3c, the recess 42 extends inwardly from the cutting edge 40 and from the distal edge 38. The recess 42 forms a relatively dull stopping edge 44 and a relatively dull measuring edge 46. The blade 34 also has a relatively dull trailing edge 50.

Preferably, and as shown, the cutting edge 40 extends to the measuring edge 46; the measuring edge 46 is generally perpendicular with respect to the cutting edge 40 and extends to the stopping edge 44; the stopping edge 44 is generally perpendicular with respect to the measuring edge 46 and is generally parallel with respect to and facing in the same leading direction as the cutting edge 40, and extends to the distal edge 38; and the distal edge 38 is generally perpendicular with respect to the stopping edge 44 and is generally parallel with respect to and facing in the same direction as the measuring edge 46, and extends to the trailing edge 50. Accordingly, the trailing edge 50 is parallel with and facing in the opposite direction to the cutting edge 40.

Preferably, the cutting edge extends a predetermined length ($L_1$) of about 500 to about 700 microns, the measuring edge extends a predetermined length ($L_2$) of about 250 to about 750 microns, and the stopping edge extends a predetermined length ($L_3$) of about 125 to about 200 microns. More preferably, the predetermined length of the cutting edge ($L_1$) is about 600 microns, the predetermined length of the measuring edge ($L_2$) is about 500 microns, and the predetermined length of the stopping edge ($L_3$) is about 150 microns.

With the knife blade 34 as described, a generally radial incision 26 previously made in the cornea 12 of an eye 10 is extended centripetally to create a smaller optical zone 24b by the following method.

As an initial step, the previously made incision 26 must be reopened. As is well known, this may be done with a blunt instrument such as the back of a blade, or a Sinskey hook.

If a first enhancement procedure as described above has not already been performed, the bottom 28 of the previously made incision 26 may be flattened out. Of course, if the original procedure has already produced a flattened bottom 28, the aforementioned step is not necessary.

The incision 26 should now be ready to be extended centripetally (the Russian technique) by the knife 32. The intended extension of the incision 26 is defined by the dashed line 51 in FIGS. 3a–3c.

As shown in FIG. 3a, the blade 34 of the knife 32 is inserted into the incision 26 with the cutting edge 40 facing centripetally, or towards the optical zone 24a. Additionally, the distal edge 38 of the blade 34 contacts the flattened bottom 28 of the incision 26. Since the distal edge 38 is relatively dull, the danger of accidental perforation into the anterior chamber 23 adjacent the cornea 12 is minimized.

As shown in FIG. 3b, the blade 34 is advanced centripetally toward and through the initial optical zone 24a. In doing so, the cutting edge 40 cuts through an upper portion 52 of the cornea 12, and the incision 26 is extended.

As can be seen in FIGS. 3b and 3c, the incision 26 may be extended until the stopping edge 44 abuts the initial wall 30a at a lower portion 54 of the cornea 12. At this point, the relatively dull stopping edge 44 prevents the knife blade 34 from cutting any further toward the smaller optical zone 24b.

In use, an optical zone marker (not shown) may be employed to make a mark (also not shown) on the cornea 12 of the eye 10. The mark is then used as a reference to indicate the end of the extension of an incision 26. Alternatively, and as shown in FIG. 3c, the knife blade 34 may be fully advanced until the relatively dull stopping edge 44 abuts the lower portion 54 of the initial wall 30a. As can be seen, the latter method extends the incision 26 a precise predetermined length $L_2$ equal to the predetermined length $L_2$ of the measuring edge 46 of the blade 34. In either method, the incision 26 is extended a distance no greater than when the stopping edge 44 abuts the initial wall 30a and prevents further extension.

Once the incision 26 is extended to an extended wall 30b, the lower portion 54 of the cornea 12 corresponding to the extension must be cut, as shown in FIG. 3d. Typically, the surgical knife 32 is removed from the incision 26 and replaced with a blade 56 suitable for this purpose. The blade 56 is then used to even out the uneven bottom portion of the extended incision 26 and to square off the wall 30b. Although a particular blade 56 is shown in FIG. 3d, it will be recognized that several different appropriate blades 56 and several different appropriate methods for evening and squaring off may be employed.

If further inward extension to incision 26 is necessary, the procedure can be repeated.

Thus, the knife 32 of the present invention provides surgical precision in RK enhancement surgery without the need for footplates or for measuring implements such as micrometer mechanisms. Since the knife cannot further deepen the incision, no guards are required. Additionally, the risk of cutting across the central optical zone and the risk of creating a second, false pass originating from within the initial incision are eliminated, while allowing precise enhancements in quanta of 500 microns or less. Moreover, the elimination of micrometer mechanisms, footplates, and/or guards effects a savings in costs and allows better visualization of the operative site by the surgeon. One skilled in the art will recognize, however, that footplates, micrometer mechanisms, and/or guards could be used, if desired.

In the foregoing description, it can be seen that the present invention comprises a new and useful surgical knife and method for performing radial keratotomy enhancement surgery. It will be appreciated by those skilled in the art that changes could be made to the embodiment described above without departing from the broad inventive concepts thereof. It is understood, therefore, that this invention is not limited to the particular embodiment disclosed, but it is intended to cover modifications within the spirit and scope of the present invention as defined by the appended claims.

I claim:

1. A surgical knife for use in radial keratotomy enhancement surgery on an eye having a cornea and a central optical zone, wherein a generally radial incision previously made in the cornea is to be extended centripetally toward the optical zone, the previously made incision having a wall adjacent the optical zone, the knife comprising a knife blade with an end, the blade having a sharpened cutting edge facing in a leading direction, a recess extending inwardly from the cutting edge and from the end of the blade, and a stopping edge at the recess, the stopping edge facing in the leading direction, the knife blade further comprising a measuring edge at the recess, the measuring edge having a predetermined length and extending from the cutting edge to the stopping edge, whereby the knife may be inserted into the previously made incision with the cutting edge facing centripetally and advanced toward the optical zone to extend the incision up to a maximum distance when the stopping edge abuts the wall and prevents further extension, the maximum distance being defined by the predetermined length of the measuring edge.

2. The surgical knife according to claim 1 wherein the end of the blade is generally rectangular and the recess is generally rectangular.

3. The surgical knife according to claim 1 wherein the cutting edge extends to the measuring edge, and wherein the stopping edge extends from the measuring edge to the end of the blade.

4. The surgical knife according to claim 3 wherein the cutting edge extends a predetermined length of about 500 to about 700 microns (micrometers), the predetermined length of the measuring edge is about 250 to about 750 microns, and the stopping edge extends a predetermined length of about 125 to about 200 microns.

5. The surgical knife according to claim 4 wherein the predetermined length of the cutting edge is about 600 microns, the predetermined length of the measuring edge is about 500 microns, and the predetermined length of the stopping edge is about 150 microns.

6. The surgical knife according to claim 1 wherein the cutting edge is generally parallel with respect to the stopping edge and the measuring edge is generally perpendicular with respect to the cutting edge and the stopping edge.

7. A method of performing radial keratotomy enhancement surgery on an eye having a cornea and a central optical zone, wherein a generally radial incision previously made in the cornea is to be extended centripetally toward the optical zone, the previously made incision having a wall adjacent the optical zone, the method comprising the steps of:

(a) inserting a surgical knife into the previously made incision, the knife comprising a knife blade with a distal edge, the blade having a sharpened cutting edge facing centripetally, a recess extending inwardly from the cutting edge and from the end of the blade, and a stopping edge at the recess, the stopping edge facing centripetally, the distal edge contacting a bottom portion of the incision;

(b) advancing the knife toward the optical zone; and (c) extending the incision a distance no greater than when the stopping edge abuts the wall and prevents further extension.

8. The method according to claim 7 wherein the inserting step comprises inserting a surgical knife into the previously made incision, the knife comprising a knife blade with an end, the blade having a sharpened cutting edge facing in a leading direction, a recess extending inwardly from the cutting edge and from the end of the blade, a stopping edge at the recess, the stopping edge facing in the leading direction, and a measuring edge at the recess, the measuring edge having a predetermined length and extending from the cutting edge to the stopping edge, the end of the blade contacting a bottom portion of the incision and the cutting edge facing centripetally, and wherein the extending step comprises extending the incision a distance no greater than the predetermined length of the measuring edge.

9. The method according to claim 8 wherein the extended incision has an uneven bottom portion, the method further comprising the steps of:
 (a) removing the surgical knife from the extended incision; and
 (b) evening out the uneven bottom portion of the extended incision.

* * * * *